(12) United States Patent
Changeux et al.

(10) Patent No.: US 10,451,256 B2
(45) Date of Patent: Oct. 22, 2019

(54) LIGHTING APPLIANCE WITH REMOVABLE HANDLE

(71) Applicant: Maquet SAS, Ardon (FR)

(72) Inventors: Patrice Changeux, Ardon (FR); Andre Loiseau, Ardon (FR)

(73) Assignee: MAQUET SAS (FR)

( * ) Notice: Subject to any disclaimer, the term of this patent is extended or adjusted under 35 U.S.C. 154(b) by 0 days.

(21) Appl. No.: 15/771,506

(22) PCT Filed: Aug. 23, 2016

(86) PCT No.: PCT/FR2016/052106
§ 371 (c)(1),
(2) Date: Apr. 27, 2018

(87) PCT Pub. No.: WO2017/089661
PCT Pub. Date: Jun. 1, 2017

(65) Prior Publication Data
US 2018/0340679 A1    Nov. 29, 2018

(30) Foreign Application Priority Data
Nov. 26, 2015  (FR) ...................... 15 61411

(51) Int. Cl.
*F21V 21/40* (2006.01)
*F21V 17/18* (2006.01)
(Continued)

(52) U.S. Cl.
CPC ............ *F21V 21/403* (2013.01); *A61B 90/30* (2016.02); *F16B 21/12* (2013.01); *F21V 17/16* (2013.01);
(Continued)

(58) Field of Classification Search
CPC ......... A61B 90/30; F16B 21/20; F21V 17/16; F21V 17/162; F21V 17/18; F21V 21/403
See application file for complete search history.

(56) References Cited

U.S. PATENT DOCUMENTS 3,075,071 A    1/1963 Lauterbach
4,316,237 A    2/1982 Yamada et al.
(Continued)

FOREIGN PATENT DOCUMENTS

CN         1661274 A      8/2005
CN    101 769 482 A      7/2010
(Continued)

OTHER PUBLICATIONS

Japanese Office Action dated Apr. 2, 2019 from corresponding JP Application No. 2018-524775 together with English language summary, 5 pages.
(Continued)

*Primary Examiner* — Robert J May
*Assistant Examiner* — Leah Simone Macchiarolo
(74) *Attorney, Agent, or Firm* — Ware, Fressola, Maguire & Barber LLP

(57) ABSTRACT

A lighting appliance (1) comprises a light module (2) having a base (6) designed to receive a handle (5) provided with a grip stick (10), the handle (5) being arranged such that it can be inserted axially in removable manner into a ring (7, 7') arranged on the base (6). The handle (5) is withdrawn axially from the base (6) by turning the ring (7, 7') relative to the base (6).

20 Claims, 4 Drawing Sheets

(51) Int. Cl.
*F16B 21/02* (2006.01)
*F21V 17/16* (2006.01)
*A61B 90/30* (2016.01)
*F16B 21/12* (2006.01)
*F21W 131/205* (2006.01)
*F16B 21/16* (2006.01)
*F16B 21/18* (2006.01)

(52) U.S. Cl.
CPC ............ *F21V 17/162* (2013.01); *F21V 17/18* (2013.01); *A61B 2090/308* (2016.02); *F16B 21/02* (2013.01); *F16B 21/16* (2013.01); *F16B 21/186* (2013.01); *F21W 2131/205* (2013.01)

(56) References Cited

U.S. PATENT DOCUMENTS

| | | | |
|---|---|---|---|
| 4,844,252 A | 7/1989 | Barron et al. | |
| 4,878,156 A * | 10/1989 | Hallings | F21V 21/403 362/109 |
| 5,485,319 A * | 1/1996 | Lemons | F21V 5/02 359/710 |
| 5,493,757 A | 2/1996 | Horan et al. | |
| 5,604,955 A | 2/1997 | Horan | |
| 6,370,735 B1 | 4/2002 | Horan et al. | |
| 2003/0014834 A1 | 1/2003 | Naughton | |
| 2003/0210559 A1 * | 11/2003 | Jesurun | F21V 21/403 362/572 |
| 2011/0317411 A1 | 12/2011 | Lee | |
| 2012/0043915 A1 * | 2/2012 | Rohwedder | F21V 21/40 315/362 |
| 2017/0030573 A1 * | 2/2017 | Alexanderson | G01S 15/88 |
| 2018/0147020 A1 * | 5/2018 | Strolin | F21V 21/40 |

FOREIGN PATENT DOCUMENTS

| | | |
|---|---|---|
| CN | 202432464 U | 9/2012 |
| CN | 202947099 U | 5/2013 |
| CN | 104214557 A | 12/2014 |
| CN | 104214602 A | 12/2014 |
| EP | 1 568 934 A1 | 8/2005 |
| JP | S49-022993 B | 6/1974 |
| JP | S56-050414 U | 10/1982 |
| JP | S59-121507 U | 8/1984 |
| JP | S63-167105 A | 7/1988 |
| JP | H04 312457 A | 11/1992 |
| JP | H04-326260 A | 11/1992 |

OTHER PUBLICATIONS

EP Office Action dated Jul. 24, 2019 issued by EPO in corresponding EP Patent Application No. 16770051.7, 7 pages.

CN Office Action dated Jul. 16, 2019 from corresponding Chinese Patent Application No. 20168006868.0, with English translation, 14 pages.

* cited by examiner

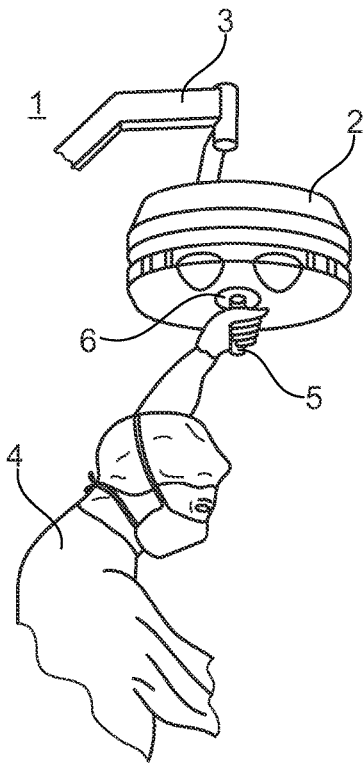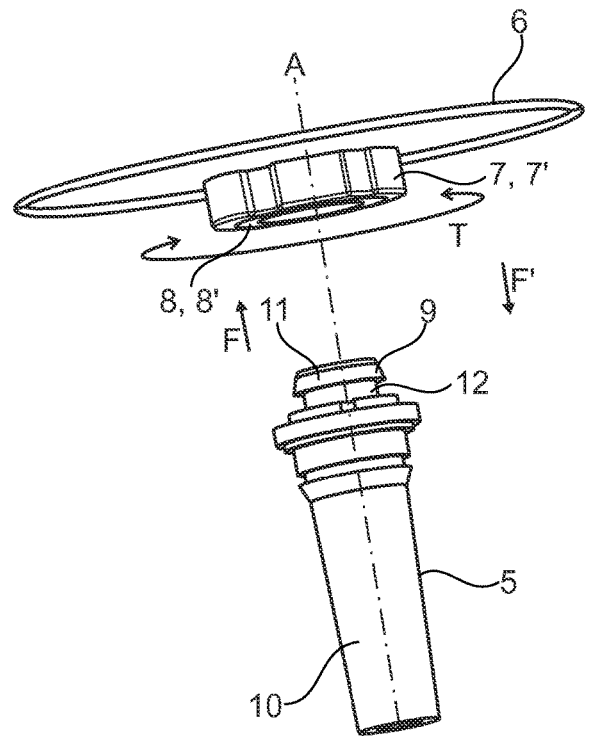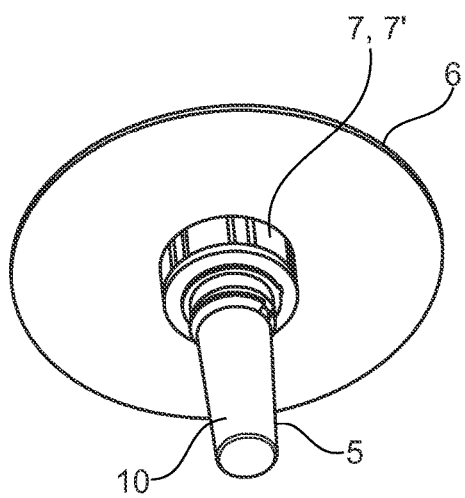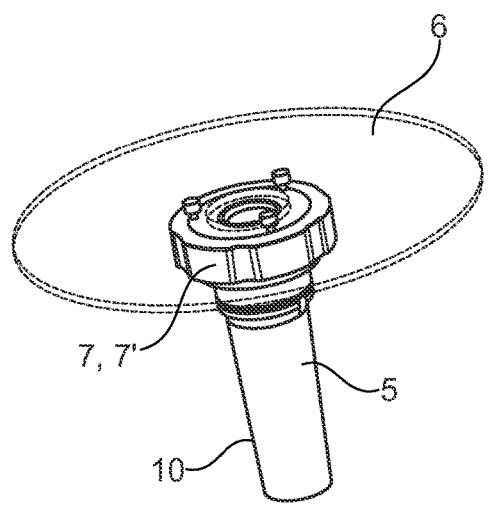
Fig. 1
Fig. 2
Fig. 3A
Fig. 3B

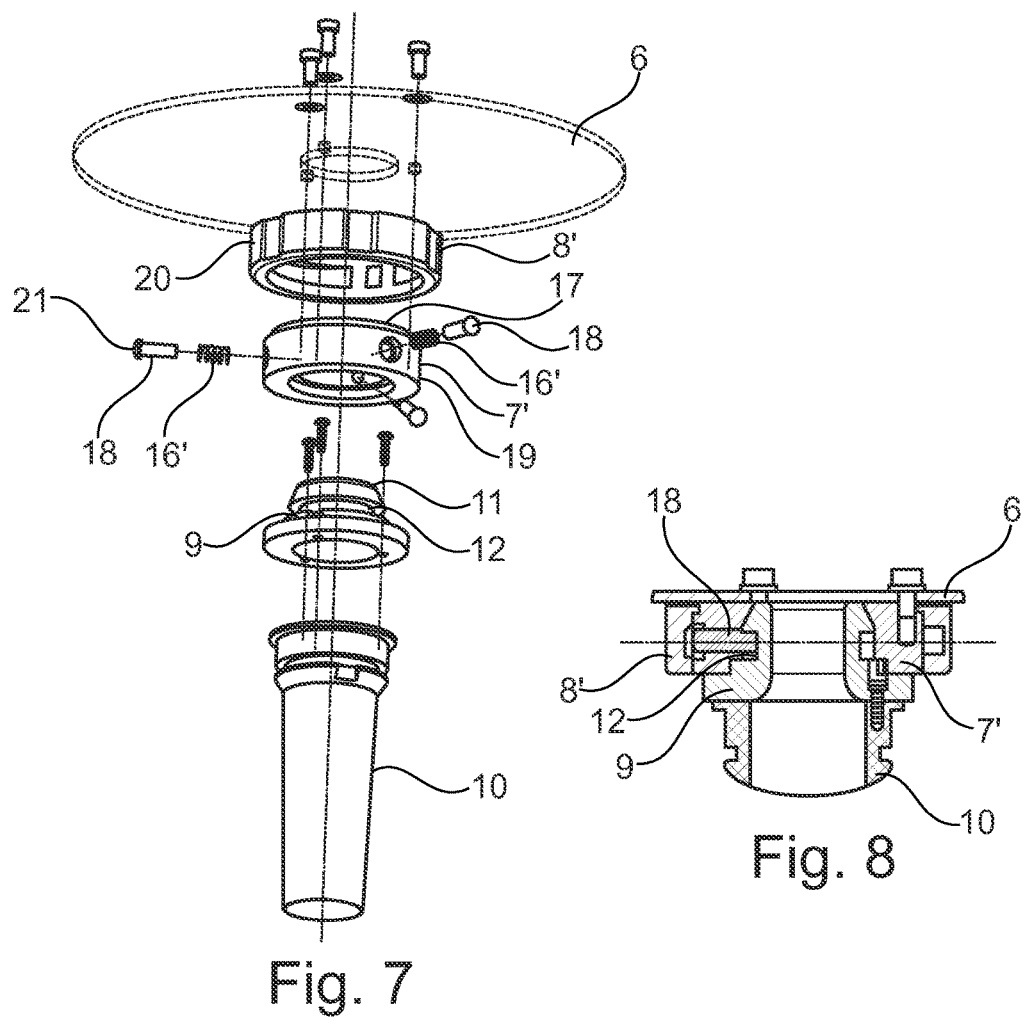
Fig. 7
Fig. 8
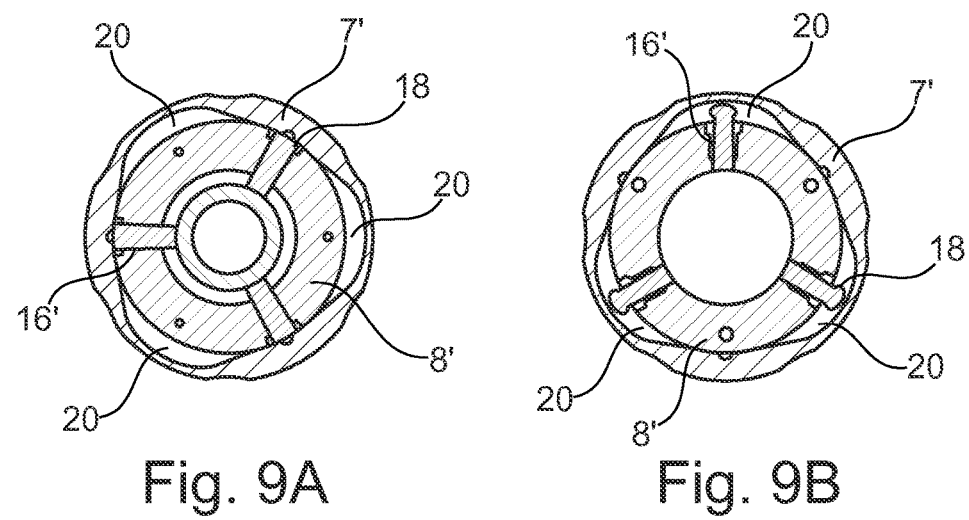
Fig. 9A  Fig. 9B

LIGHTING APPLIANCE WITH REMOVABLE HANDLE

CROSS REFERENCE TO RELATED APPLICATIONS

This application is the U.S. National Stage of International Application Number PCT/FR2016/052106 filed on Aug. 23, 2016, which application claims priority under 35 USC § 119 to French Patent Application No. 1561411 filed on Nov. 26, 2015. Both applications are hereby incorporated by reference in their entirety.

TECHNICAL FIELD

The invention relates generally to a lighting appliance that comprises a light module having a base designed to receive a handle provided with a grip stick, the handle being arranged such that it can be inserted axially in removable manner into a ring arranged on the base.

PRIOR ART

In known manner, a lighting appliance used in an operating theater for illuminating an operative field comprises a light module attached to a suspension arm so as to be positionable above the operative field. The position of the light module can be modified by the medical team in the operating theater. For the purpose of maneuvering the light module so as to modify its position, it is provided with a handle enabling it to be moved and steered in the space above the operative field.

It is currently common practice to provide sterile handles and sterile handle covers or shields that are touched by staff in the medical team while the light module is being manipulated during an operation.

Documents U.S. Pat. Nos. 4,844,252 and 6,370,735 disclose sterile handles that are connectable in removable manner to a surgical lighting light module. Such a handle has an upper portion that is threaded for being screwed into a socket arranged on the structure of the lighting module.

In an operating theater, in order to maintain sterility, it is necessary to limit the manipulations and the surfaces that are touched, by facilitating connections between various items of medical equipment. Unfortunately, with known handles, mounting the handle on the lighting module and removing it therefrom requires a large amount of torque to be applied during screwing and unscrewing. Furthermore, during those screwing and unscrewing operations, in addition to holding the handle via a stick, the medical staff must also touch the lighting module in order to hold it in place because it is arranged on a suspension arm that moves.

SUMMARY OF THE INVENTION

An object of the invention is to remedy those drawbacks by proposing a lighting appliance enabling a sterile handle to be mounted on it and removed from it easily and quickly.

More particularly, the invention provides a lighting appliance comprising a light module having a base designed to receive a handle provided with a grip stick, the handle being arranged such that it can be inserted axially in removable manner into a ring arranged on the base, the lighting appliance being characterized in that the handle may be withdrawn axially from the base by turning the ring relative to the base.

The medical lighting appliance of the invention may, in particular have any of the following features:

- a latch may be received in the ring for the purpose of locking and unlocking the handle in the base;
- the latch may be provided with at least one retractable cam;
- the latch may be provided with two cams mounted on springs so that the springs press the cams so as to lock the handle in the base, and so that, when the ring is turned, the springs may be compressed by the cams as pushed by lugs arranged on the inside surface of the ring;
- the latch may be provided with at least one retractable stud extending radially;
- the latch may be provided with three studs mounted on springs so that the studs project into the ring to lock the handle in the base and so that, when the ring is turned, the studs are in a retracted position in which they are retracted into respective recesses arranged in the inside surface of the ring;
- the handle may be provided with a fastening head having a positioning protuberance of convex shape for positioning in the ring, the protuberance having an annular groove arranged to be able to co-operate with the latch;
- the handle may be sterile; and
- an electrical appliance may be received in the handle, and means for electrically powering and monitoring/controlling the electrical appliance may be arranged on the handle and on said base.

With this arrangement of the invention, a medical lighting appliance is obtained on which it is possible for a sterile handle to be mounted quickly by snap-fastening onto a base of the lighting appliance, and for the handle to be locked/unlocked easily in the base by means of a rotary ring on the base of the lighting appliance, which ring is easy for the medical staff to turn relative to the base.

In accordance with the invention, adding a latch in the ring makes it possible to co-operate with the handle so that, when the ring is in the locking position, it is possible to retain the handle in the base, and, when the ring is in the unlocking position, it is possible to allow the handle to be withdrawn. The latch is provided with retractable retaining means, based on cams or studs, mounted on springs so that they project into or are retracted from the orifice of the ring depending on the position of the rotary ring.

With the lighting appliance of the invention, the manipulations of the appliance and the surfaces touched by the medical staff for connecting a handle are respectively facilitated and limited.

BRIEF DESCRIPTION OF THE DRAWINGS

The present invention can be better understood and other advantages appear on reading the following description and on examining the accompanying drawings, in which:

FIG. 1 is a diagrammatic view of a medical lighting appliance of the invention that is manipulated by an operator via a handle;

FIG. 2 is a perspective view of a handle that can be mounted on and removed from a base of a lighting appliance of the invention;

FIG. 3A is a perspective view of a handle that can be mounted on a lighting appliance of the invention;

FIG. 3B is another perspective view of a handle that can be mounted on a lighting appliance of the invention;

FIG. 7 is an exploded perspective view of a base of a medical lighting appliance and of a handle in a second embodiment of the invention;

FIG. 8 is a profile view in longitudinal section of a portion of a handle mounted in a base of a medical lighting appliance in a second embodiment of the invention;

FIGS. 9A and 9B are cross-section views respectively showing the unlocking and locking positions of the base for a handle of a medical lighting appliance in a second embodiment of the invention.

DETAILED DESCRIPTION

Figure 4:
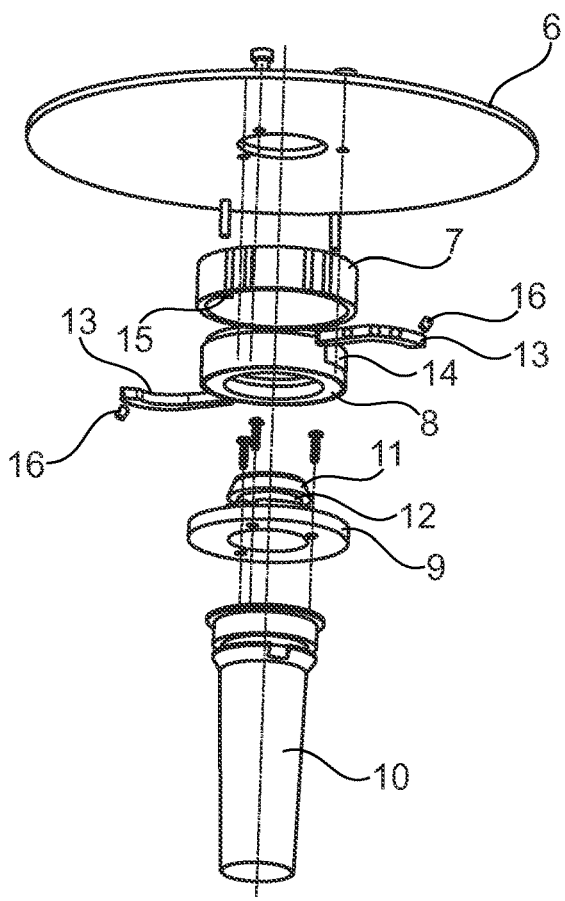
FIG. 4 is an exploded perspective view of a base of a medical lighting appliance and of a handle in a first embodiment of the invention.

FIG. 1 shows a portion of a medical lighting appliance 1 used in an operating theater, with a light module 2 attached to an articulated suspension arm 3, so that the light module 2 can be positioned adjustably above an operative field (not shown) and so that said operative field can be illuminated appropriately. In this example, a member of the medical staff 4 such as a surgeon maneuvers the light module 2, by using a handle 5, so as to move it and steer it above the operative field.

The handle 5 is connected removably to the light module 2 via a base 6, arranged in this example in a manner such that it is centered on a bottom face of the light module 2.

The base 6 shown in this example is in the form of a flat disk. One of the faces of the disk is fastened by any known means to the light module 2. As can be seen in FIG. 2, a fastening system for fastening the handle 5 into the base 6 is arranged on the other face of the disk. The fastening system is made up of a ring 7, 7' arranged on the base 6 in such a manner that said ring can turn about an axis A perpendicular to the surface of the disk of the base 6, in either direction as indicated by double-headed arrow T.

The orifice formed by the ring 7, 7' receives a latch 9, 9' that is axially engageable into the ring 7, 7' and that is described below. The latch 8, 8' is designed to hold the handle 5 in the base 6 when the handle 5 is inserted axially as indicated by arrow F into the ring 7, 7' and to enable the handle 5 to be withdrawn axially from the base 6 as indicated by arrow F' by turning the ring 7, 7'.

The handle 5 comprises a fastening head 9 carried by one of the ends of a grip stick 10.

FIGS. 3A and 3B show the handle 5 snap-fastened in the base 6, the fastening head 9 of the handle 5 being in engagement in the ring 7, 7' and being held in the ring 7, 7' via the latch 8, 8'. The handle 5 remains accessible via the grip stick 10.

As can be seen in FIGS. 2, 4, and 7, the fastening head 9 comprises a bed in the form of a disk with a positioning protuberance 11 extending axially. In this example, the positioning protuberance 11 is of convex shape so as to facilitate insertion of the fastening head 9 into the orifice in the ring 7, 7', and is provided with an annular groove 12 that co-operates with the latch 8, 8' to hold the handle 5 in the orifice in the ring 7, 7'.

FIGS. 9 to 6 show a first embodiment of a manner in which the handle 5 is removably snap-fastened into the base 6, and FIGS. 7 to 9 show a second embodiment of a manner in which the handle 5 is removably snap-fastened into the base 6. The elements that are common to both of the embodiments bear like references.

FIG. 4 is an exploded view of a first embodiment of a manner in which the handle 5 is snap-fastened into the base 6 in removable manner. In this embodiment, the latch 8 is of annular shape, and of outside diameter slightly less than the inside diameter of the ring 7. The annular shape of the latch 8 has two spirally shaped cams 13 arranged symmetrically, each of which is mounted to pivot at one of its ends on the circumference of the annular shape, and the cams extending in respective openings 14 along the circumference of the annular shape.

Figure 6A:
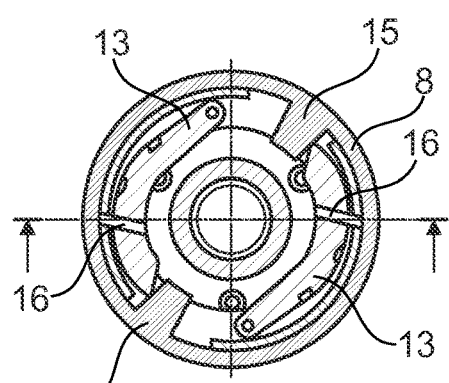
FIGS. 6A and 6B are cross-section views respectively showing the unlocking and locking positions of the base for a handle of a medical lighting appliance in a first embodiment of the invention.
Figure 6B:
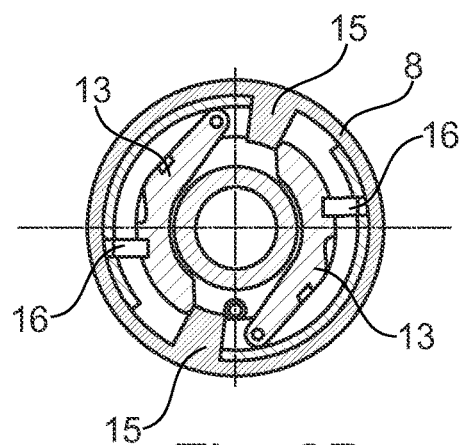

In this example, on its inside surface, the ring 7 has two radially projecting lugs 15 that are arranged symmetrically (and that can be seen in FIGS. 6A and 6B).

Figure 5A:
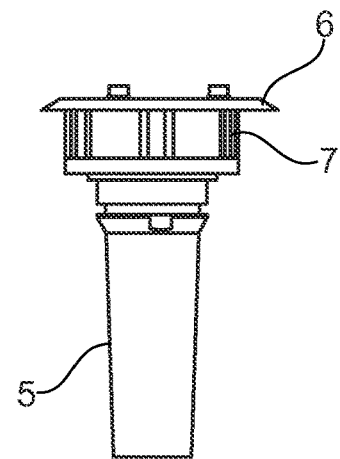
FIG. 5A is profile view of a handle mounted in a base of a medical lighting appliance in a first embodiment of the invention.
Figure 5B:
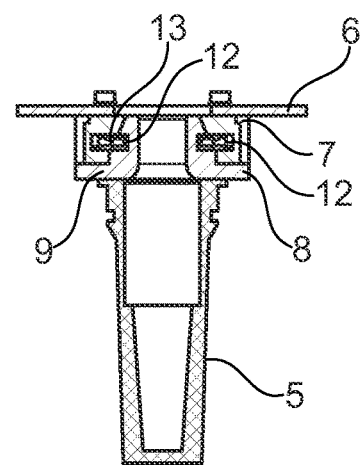
FIG. 5B is a longitudinal section view of FIG. 5A.

FIGS. 5A and 5B show the handle 5 as mounted in the base 6 of the lighting appliance in the first embodiment, with the ring 7 in the locking position.

FIGS. 6A and 6B show the principle of how the latch 8 operates as a function of the position of the ring 7, i.e. depending on whether it is in the locking position (FIG. 6B) or in the unlocking position (FIG. 6A).

When the latch 8 is received in the ring 7, a spring 16 is present in the space between the free end of each of the cams 13 and the inside surface of the ring 7 so that, when the ring 7 is in the locking position (FIG. 6B), the cams 13 project into the orifice in the latch 8 through the openings 14 in the latch. When the ring 7 is in the unlocking position (FIG. 6A), the lugs 15 in the ring 7 bear against the free ends of the cams 13, thereby causing the cams 13 to retract into the openings 14 in the latch 8 and causing the springs 16 to be compressed between the free ends of the cams 13 and the inside surface of the ring 7.

FIG. 7 is an exploded view of a second embodiment of a manner in which the handle 5 is snap-fastened into the base 6 of the lighting appliance 1 in removable manner. In this embodiment, the latch 8' is also of annular shape, of outside diameter slightly less than the inside diameter of the ring 7'.

In this example, the latch has three orifices 17 disposed radially and symmetrically in the wall of the latch 8' and via which studs 18, of length greater than the thickness of the latch 8', are mounted on springs 16' and are disposed in through manner.

Each of the studs 18 has a head of diameter wider than the diameter of the orifice 17.

Each orifice 17 has a shoulder 19 so that the spring 16' does not pass through the orifice 17 at the inside face of the latch 8'.

In this example, in its inside surface the ring 7' has three recesses 20 that are disposed symmetrically (and that can be seen in FIGS. 9A and 9B).

FIGS. 8 and 9A show the latch 8' as received in the ring 7' in the locking position in the second embodiment. When the ring 7' is in this locking position, the heads 21 of the studs 18 are pushed into the orifices 17 by the "uninterrupted" inside surface i.e. outside the recesses 20) of the ring 7'. The studs 18 project into the orifice in the latch 8' and the springs 16' are compressed.

FIG. 9B shows the latch 8' and the ring 7' in the unlocking position. In this unlocking position, the recesses 20 of the ring 7' find themselves facing the orifices 17 passing through the latch 8'. Urged by the springs, the studs 18 retract into those spaces so that they no longer project into the orifice in the latch 8'.

In the first embodiment described above and in accordance with the invention, when a member of the medical staff 4 wants to install a sterile handle 5 on the lighting appliance 1, that member of staff holds the handle 5 by its grip stick 10 and inserts the fastening head 9 axially into the orifice in the latch 8.

If the ring 7 is in the unlocking position, then the cams 13 are retracted in the latch 8. By turning the ring 7 into the locking position, the cams 13 mounted on springs 16 come to be received in the annular groove 12 in the fastening head 9 of the handle 5 so as to lock the handle 5 in the base 6.

It should be noted that, in this embodiment, if the ring 7 is in the locking position when the handle 5 is axially inserted, the convex shape of the fastening head 9 can push the cams 13 mounted on springs 16 so that they move apart and retract into the openings 14 in the latch 8 so as to allow the fasting head 9 to go through to the level of the annular groove 12, whereupon, the cams 13 mounted on springs 16 automatically come to be received in said annular groove 12, thereby locking the handle 5 in the base 6.

In order to remove the handle 5 from the lighting appliance 1 so as to change it, the member of the medical staff 4 takes hold of the handle 5 via the grip stick 10 with one hand, and turns the ring 7 into the unlocking position with the other hand. When the ring 7 is in this position, the lugs 15 of the ring 7 push the free ends of the cams 13 so as to compress the springs 16, thereby spacing the cams 13 apart from the orifice of the latch 8 and disengaging them from the annular groove 12 in the fastening head 9 of the handle 5. Thus, the member of the medical staff 4 can pull the handle 5 out axially to withdraw it from the base 6.

In the second embodiment described above and in accordance with the invention, when a member of the medical staff 4 wants to install a sterile handle 5 on a lighting module 2 of the lighting appliance 1, that member of staff holds the handle 5 by its grip stick 10 and inserts the fastening head 9 axially into the base 6 when the ring 7' is in the unlocking position. In this position, the studs 18 do not project into the orifice in the latch 8' and allow the fastening head 9 to pass through. Then, by turning the ring 7' into the locking position, the studs 18 mounted on springs 16' are caused to come to be received in the annular groove 12 in the fastening head 9 of the handle 5 so as to lock the handle 5 in the base 6.

In order to remove the handle 5 from the lighting appliance 1 so as to change it, the member of the medical staff 4 takes hold of the handle 5 via the grip stick 10 with one hand, and turns the ring 7' into the unlocking position with the other hand. When the ring 7' is in this position, the studs 18 mounted on springs 16' find themselves facing the recesses 20 into which they retract. The studs 18 then disengage from the annular groove 12 in the fastening head 9 of the handle 5. Thus, the member of the medical staff 4 can pull the handle 5 out axially to withdraw it from the base 6.

In a medical environment, maintaining good sterility conditions around an operative field is a priority. The lighting appliance 1 of the invention enables the member of the medical staff 4 to snap-fasten the handle 5 in removable manner by touching the grip stick 10 and the ring 7, 7' only. Thus, the touched surfaces are limited for fastening a sterile handle 5 prior to an operation and for removing it at the end of the operation. In addition, it is easy and quick both to fasten the handle 5 and to remove it. In the first embodiment, it is possible to fasten the handle 5 by pushing the handle 5 into the base 6, or by performing the simple gesture of turning the ring 7 in order to lock the handle 5. In the second embodiment, it is possible to fasten the handle 5 by performing the simple gesture of turning the ring 7' in order to lock the handle 5 in the base 6 and in order to unlock said handle 5 in said base 6.

In the first and second embodiments, in order to withdraw the handle 5 from the base 6, it suffices to turn the ring 7, 7' into the unlocking position and to pull the handle 5 out axially.

Figures 10A, 10C:
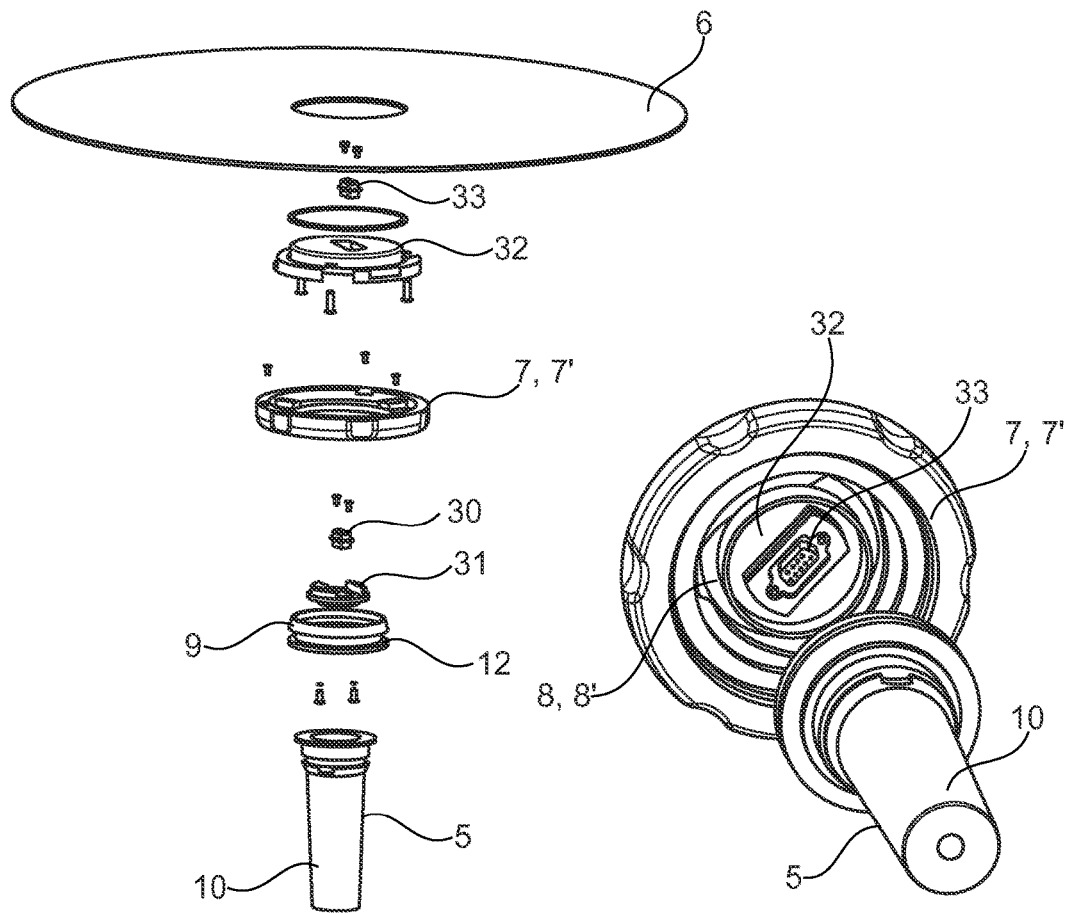
FIGS. 10A, 10B, and 10C show a removable handle adapted to receive an electrical appliance, with two views in perspective of a handle that can be mounted on and removed from a base, and one view in exploded perspective of a base of a medical lighting appliance and of a handle in a third embodiment of the invention.
Figure 10B:
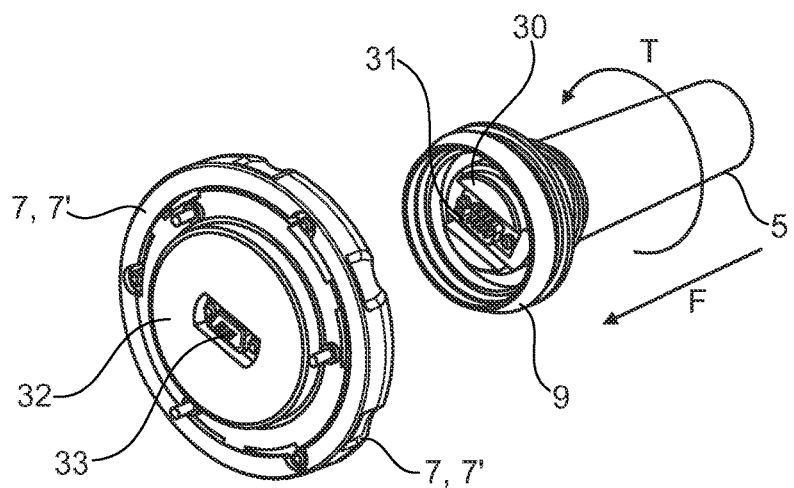

In a third embodiment of the invention that is shown in FIGS. 10A to 10C, the handle 5 may be hollow so that it can receive, for example, a camera for filming the operative field, a lamp, a multimedia appliance, or any other electrical appliance (not shown). In order to supply electrical power to and in order to monitor or control the electrical appliance received in the hollow handle 5, means for electrically powering and for monitoring/controlling the electrical appliance are arranged on the handle and on the base. In this example, the positioning protuberance 11 has a rotary connector 30 arranged on a first connector support 31.

In this particular embodiment, a second connector support 32 for a stationary connector 33 is mounted on the base 6 in such a manner that the connection between the rotary connector 31 and the stationary connector 33 takes place through the fastening system of the invention.

The handle 5 snap-fastens in removable manner as described above into the ring 7, 7' in which it is received with the latch 8, 8'.

The invention claimed is:

1. A lighting appliance comprising:
   a light module having a base configured to receive a handle provided with a grip stick, said handle being arranged such that it can be inserted axially in removable manner into a ring arranged on said base, wherein said handle is withdrawn axially from said base by turning said ring relative to said base.

2. The lighting appliance according to claim 1, wherein a latch is in said ring for the purpose of locking and unlocking said handle in said base.

3. The lighting appliance according to claim 2, wherein said latch comprises at least one retractable cam.

4. The lighting appliance according to claim 3, wherein said latch comprises two cams mounted on springs so that said springs press said cams so as to lock said handle in said base, and so that, when said ring is turned, said springs are compressed by said cams as pushed by lugs arranged on the inside surface of said ring.

5. The lighting appliance according to claim 2, wherein said latch comprises at least one retractable stud extending radially in said ring.

6. The lighting appliance according to claim 5, wherein said latch comprises three studs mounted on springs so that said studs project into said ring to lock said handle in said base and so that, when said ring is turned, said studs are in a retracted position in which they are retracted into respective recesses arranged in the inside surface of said ring.

7. The lighting appliance according to claim 6, wherein said handle comprises a fastening head having a positioning protuberance of convex shape for positioning in said ring, said protuberance having an annular groove arranged to co-operate with said latch.

8. The lighting appliance according to claim 2, wherein said handle comprises a fastening head having a positioning protuberance of convex shape for positioning in said ring, said protuberance having an annular groove arranged to co-operate with said latch.

9. The lighting appliance according to claim 1, wherein said handle is sterile.

10. The lighting appliance according to claim 1, wherein an electrical appliance is received in said handle, and in that means for electrically powering, and for monitoring and/o controlling, said electrical appliance are arranged on said handle and on said base.

11. The lighting appliance according to claim 1, wherein said handle comprises a fastening head having a positioning protuberance of convex shape for positioning in said ring, said protuberance having an annular groove arranged to co-operate with said latch.

12. The lighting appliance according to claim 1, wherein an electrical appliance is in said handle.

13. The lighting appliance according to claim 1, further comprising a camera inside the handle, the camera being oriented for filming an area being illuminated by the lighting appliance during use, wherein the camera is removable from the lighting appliance by removing the handle from the base.

14. The lighting appliance according to claim 1, wherein the lighting appliance is a medical lighting appliance for illuminating a surgical field, and wherein the lighting appliance comprises a movable suspension arm for positioning the medical appliance.

15. A medical light for illuminating and filming an operating field, the medical light comprising:
- a light module, the light module comprising a base for facing the operating field during use;
- a ring on the base, the ring having an orifice;
- a latch, the latch being in the ring;
- a handle, the handle having a camera therein positioned for filming the operating field when in use;
- wherein the orifice and the ring are configured for selectably receiving and releasing the handle, including the camera therein, using the latch;
- wherein the handle can be inserted axially into the orifice of the ring and engaged therein; and
- wherein the handle and the camera can be disengaged from the latch, for withdrawal from the orifice, by rotating the ring.

16. The medical light according to claim 15, wherein said latch comprises at least one of: at least one retractable cam, and at least one retractable stud extending radially in the ring.

17. The medical light according to claim 15, wherein the handle comprises a fastening head at an end thereof, the fastening head having a positioning protuberance of convex shape for positioning in said ring, said protuberance having an annular groove positioned to engage the latch for reversible connecting to the light module via the latch.

18. A medical light for illuminating an operating field, the medical light comprising:
- a light module, the light module comprising a base for facing the operating field during use;
- a ring on the base, the ring having an orifice;
- a latch;
- a handle, the handle being oriented towards the operating field when engaged to the light module during use;
- wherein the orifice and the ring are configured for selectably receiving and releasing the handle via the latch;
- wherein the handle can be inserted axially into the orifice of the ring and engaged therein; and
- wherein the handle can be disengaged from the latch for withdrawal from the orifice.

19. The lighting appliance according to claim 18, wherein an electrical appliance is inside said handle, wherein the electrical appliance is oriented towards the operating field when in use, and wherein the electrical appliance can be selectably added and removed from the medical light by engaging and disengaging the handle from the medical light.

20. The lighting appliance according to claim 18, wherein said latch comprises at least one of: at least one retractable cam, and at least one retractable stud extending radially in the ring, and wherein the handle and the camera can be disengaged from the latch, for withdrawal from the orifice, by rotating the ring.

* * * * *